Aug. 10, 1971 H. W. GUENGERICH Plant Pat. 3,061
APPLE TREE
Filed Aug. 27, 1969
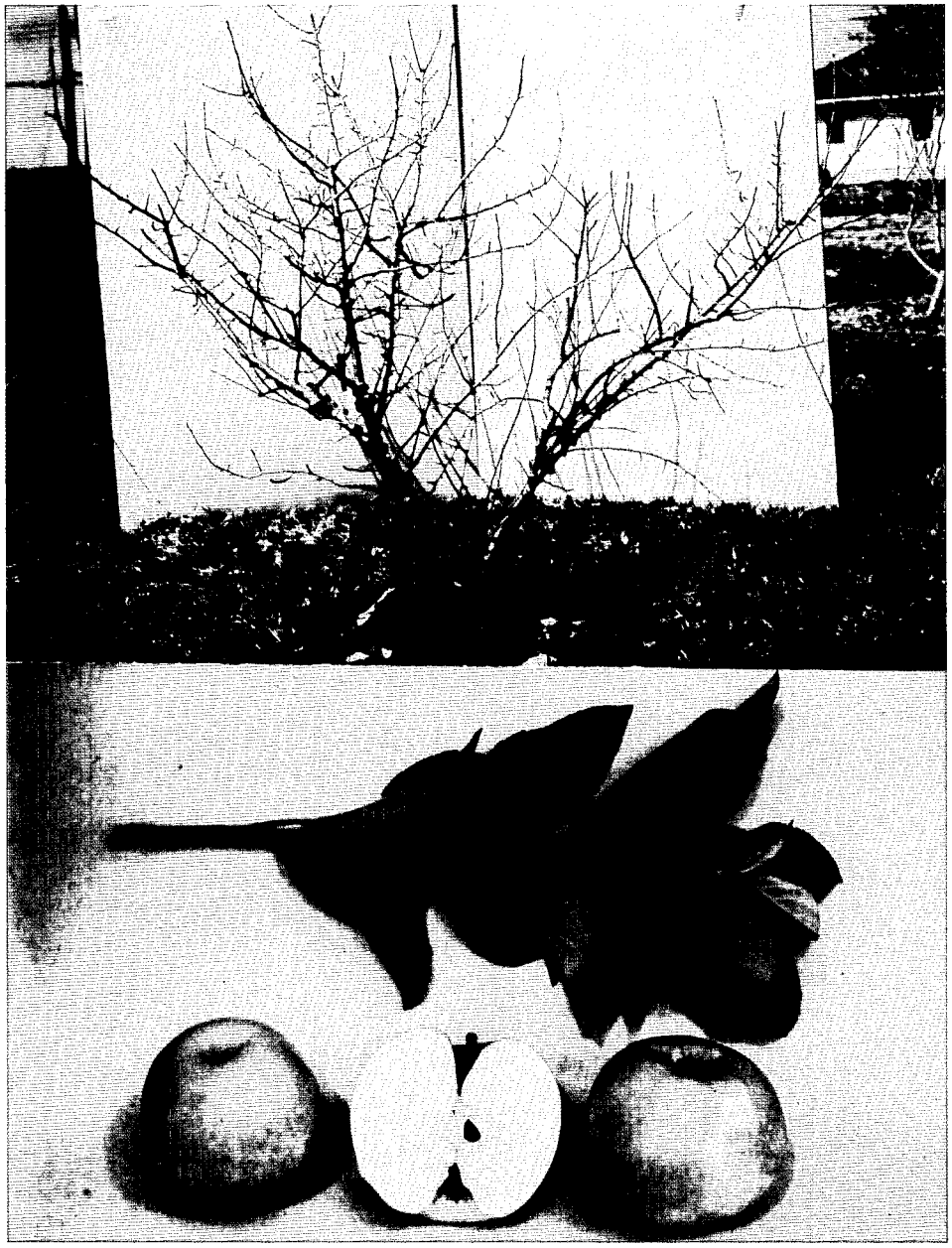
Inventor.
H. W. Guengerich
By: Robb & Robb
Attorneys.

United States Patent Office

Plant Pat. 3,061
Patented Aug. 10, 1971

3,061
APPLE TREE

Harry W. Guengerich, Louisiana, Mo., assignor to Stark Bro's Nurseries & Orchard Company, Louisiana, Mo.

Filed Aug. 27, 1969, Ser. No. 853,554
Int. Cl. A01h *5/03*
U.S. Cl. Plt.—34 1 Claim

The present invention relates to a new and distinct variety of apple tree which was discovered by me in a test orchard owned by my assignee and located near Louisiana, in Pike County, Mo., said new variety having originated as an open-pollinated seedling of the variety of apple tree known as "Clark Dwarf" (unpatented).

My new discovery resulted from a research program conducted by my assignee under my direction, and had for its primary objective the development of a new and improved variety of apple tree which would be useful as dwarfing interstock for producing dwarf apple trees having improved characteristics as compared with those produced by an unnamed and unpatented dwarfing interstock known as "EM IX" which formerly was extensively used by my assignee, but which is susceptible to stem-pitting virus. This objective was fully achieved, as evidenced by the fact that, as a tree, it grows about the same height as "EM IX," but is more vigorous and more spreading in form, and more tolerant to stem-pitting virus. Also, when the new variety is used as dwarfing interstock, it produces trees that are somewhat smaller than trees derived from the use of "EM IX" as dwarfing interstock, that is, about two-thirds the size of standard trees grown on the usual seedling rootstock, but which bear heavily and at an earlier age. All of these attributes are commercially valuable.

Asexual reproduction of my new variety by layering, as performed by me in Pike County, Mo., shows that the foregoing characteristics and distinctions come true and are established and transmitted through succeeding propagations.

The accompanying drawing shows a typical bare tree of my new variety, as well as typical specimens of its foliage and fruit, with one of the fruit specimens being shown in longitudinal cross-section, and all as depicted in color as nearly true as it is reasonably possible to make the same in a color illustration of this character.

The following is a detailed description of my new variety, with color terminology in accordance with Ridgway's Color Standards and Nomenclature, hereinafter abbreviated as (R), Horticultural Colour Guide, hereinafter abbreviated as (HCG), and Munsell Color Chart, hereinafter abbreviated as (M), except where general color terms of ordinary dictionary significance are obvious:

Location where grown and observed: Pike County, Mo.

Dates of first and last pickings: About August 1 and August 12, respectively.

Tree: Small; medium vigorous; spreading; low; open; slow growing; hardy; productive; regular bearer.

*Trunk.*—Stocky; medium shaggy.

*Branches.*—Medium thickness; much-branched. Color (shoots)—Liver Brown, Plate XIV, Color No. 7′, tone m (R). Lenticels—Numerous; medium small. Leaves—Medium small; medium wide; medium short; oval; taper-pointed; medium thickness; smooth. Length—From about 2¾ inches to 3½ inches. Width—From about 1¾ inches to 2 inches. Color—Spinach Green, Plate 0960/2, page 187, volume II (HCG). Margin—Finely serrate. Petiole—Long (from about ¾ inch to 1 inch); medium slender.

Flowers: Medium early.

*Dates of first and full bloom.*—About April 19 and 27, respectively.

Fruit:

*Maturity when described.*—Hard ripe—about August 8.

*Size.*—Uniform. Axial diameter—About 2⅞ inches. Transverse diameter—About 2 inches.

*Form.*—Globose; angular.

*Cavity.*—Symmetrical; abrupt at base; rounded toward apex; undulate; pubescent toward apex.

*Basin.*—Symmetrical; abrupt at base; undulate. Depth—About 9/16 inch. Breadth—About ⅞ inch. Markings—Russeted with Old Gold, Plate XVI, Color No. 19′, tone i (R).

*Stem.*—Slender; pubscent. Length—About ⅞ inch. Breadth—About 1/16 inch. Markings—None.

*Calyx.*—Some open and some closed; segments persistent; acute; about 9/64 inch long; approximate at base; erect; reflexed from base at apex; pubescent on both outer and inner surfaces.

*Skin.*—Thin; tough; some smooth and some rough; waxed. Dots—Conspicuous; few; small; raised; ruptured; circular. Color—Wood Brown, Plate XL, Color No. 17‴ (R). Distribution—Rather evenly over entire surface. Ground color—Brilliant Yellow Green, Hue 2.5 GY 9/8 (M). Color markings—Striped; dull. Color—Carmine, Plate 21/1, page 21, volume I (HCG). Bloom—Wanting. Scarfskin—Color—Light gray. General color effect—Bright red, dulled by gray scarfskin, with yellowish-green ground color.

*Flesh.*—Rather dry. Color—White. Texture—Hard; fine; crisp. Flavor—Acid. Aroma—Wanting. Quality—Inferior.

*Core.*—Median. Bundle area—Large; oblate; symmetrical at base. Halves of core—Unequal. Bundles—Inconspicuous; in one whorl. Color—Green. Core lines—Clasping. Cross section—Indistinct. Carpellary area—Indistinct. Calyx tube—Glabrous toward base; urn-shaped at apex. Entire depth—¼ inch.

*Styles.*—Present; fleshly at base; united toward base; pubescent throughout.

*Stamens.*—Median; in one distinct whorl.

*Seed cells.*—Closed. Cell walls—Approximate; thick; tough. Length—About ½ inch. Breadth—About ⅜ inch. Longitudinal section—Orbicular; obtuse at apex. Surface—Entire; smooth. Cross section—Narrow.

Seeds:

*Average number.*—From 6 to 8 perfect; 2 per cell.

*Length.*—About 5/16 inch.

*Breadth.*—About 3/16 inch.

*Form.*—Acute.

*Color.*—Van Dyke Brown, Plate XXVIII, Color No. 11″, tone m (R).

Use: Fruit worthless, but woody stems useful as good dwarfing interstock.

Disease resistance: Good tolerance to stem-pitting virus, as determined from comparison with other varieties grown under comparable conditions in Pike County, Mo.

I claim:

1. A new and distinct variety of apple tree, substantially as herein shown and described, characterized particularly as to novelty by a more vigorous and more spreading tree habit than the variety identified as "EM IX" formerly used extensively as dwarfing interstock, and having greater tolerance to stem-pitting virus than "EM IX," said new variety also having superior utility as dwarfing interstock to produce dwarf apple trees about two-thirds the size of standard trees grown on the usual seedling rootstock, but which bear earlier and heavily.

No references cited.

ROBERT E. BAGWILL, Primary Examiner